United States Patent
Wei et al.

(10) Patent No.: US 9,445,838 B2
(45) Date of Patent: Sep. 20, 2016

(54) PEN NEEDLE ASSEMBLY FOR DELIVERING DRUG SOLUTIONS

(75) Inventors: Min Wei, Morris Plains, NJ (US); Robert Banik, Long Valley, NJ (US); Michael Di Biasi, West Milford, NJ (US); Roger W. Groskopf, Saddle Brook, NJ (US)

(73) Assignee: Bection, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/138,549

(22) PCT Filed: Mar. 3, 2010

(86) PCT No.: PCT/US2010/026129
§ 371 (c)(1),
(2), (4) Date: Dec. 13, 2011

(87) PCT Pub. No.: WO2010/102067
PCT Pub. Date: Sep. 10, 2010

(65) Prior Publication Data
US 2012/0109052 A1   May 3, 2012

Related U.S. Application Data

(60) Provisional application No. 61/209,050, filed on Mar. 3, 2009.

(51) Int. Cl.
*A61M 5/32*   (2006.01)
*A61M 5/46*   (2006.01)
(Continued)

(52) U.S. Cl.
CPC ........ *A61B 17/3496* (2013.01); *A61M 5/3202* (2013.01); *A61M 5/329* (2013.01);
(Continued)

(58) Field of Classification Search
CPC .... A61M 5/3293; A61M 5/329; A61M 5/46; A61M 25/0097; A61M 5/425; A61M 5/3202
USPC .......................................................... 604/117
See application file for complete search history.

(56) References Cited

U.S. PATENT DOCUMENTS

| 3,739,779 A | * | 6/1973 | Pfleger .......................... 604/205 |
| 3,961,622 A | | 6/1976 | Edwards |

(Continued)

FOREIGN PATENT DOCUMENTS

| CN | 1571685 A | 1/2005 |
| CN | 1859937 A | 11/2006 |

(Continued)

OTHER PUBLICATIONS

Notice of Rejection Issued in JP Patent Application No. 2011-553096 dated Dec. 17, 2013.
(Continued)

*Primary Examiner* — Theodore Stigell
*Assistant Examiner* — Benjamin Koo
(74) *Attorney, Agent, or Firm* — Dickinson Wright PLLC

(57) ABSTRACT

In one aspect, a pen needle assembly is provided herein which includes a hub, and a needle fixed to the hub, the needle having proximal and distal ends with a lumen extending therebetween. The needle extends distally from the hub to define an exposed length between the distal end of the needle and the hub in the range of about 5.0 to 9.0 mm. The hub defines a post formed about the needle, the post having a distally-facing first skin engaging surface. The exposed length of the needle extends distally from the first skin engaging surface. The hub also defines a distally-facing second skin engaging surface which at least partially circumscribes the first skin engaging surface. The second skin engaging surface being located proximally of the first skin engaging surface. Advantageously, with the subject invention, a pen needle assembly is provided having two skin engaging surfaces which provide stability in achieving subcutaneous injections.

13 Claims, 5 Drawing Sheets

(51) Int. Cl.
*A61B 17/34* (2006.01)
*A61M 5/00* (2006.01)
*A61M 5/34* (2006.01)
*A61M 5/42* (2006.01)

(52) U.S. Cl.
CPC .......... *A61M 5/3293* (2013.01); *A61M 5/46* (2013.01); *A61M 5/002* (2013.01); *A61M 5/347* (2013.01); *A61M 5/425* (2013.01); *Y10T 29/49815* (2015.01)

(56) References Cited

U.S. PATENT DOCUMENTS

| | | | |
|---|---|---|---|
| 5,098,389 A | 3/1992 | Cappucci | |
| 5,941,857 A * | 8/1999 | Nguyen et al. | 604/263 |
| 5,944,700 A | 8/1999 | Nguyen | |
| 6,387,074 B1 | 5/2002 | Horppu et al. | |
| 6,595,960 B2 * | 7/2003 | West et al. | 604/181 |
| 6,986,760 B2 | 1/2006 | Giambattista | |
| 7,556,615 B2 | 7/2009 | Pettis et al. | |
| 7,842,008 B2 * | 11/2010 | Clarke | A61M 5/158 604/115 |
| 8,133,202 B2 * | 3/2012 | Marsh | 604/117 |
| 8,241,257 B2 * | 8/2012 | Wei | 604/242 |
| 2003/0050602 A1 | 3/2003 | Pettis et al. | |
| 2007/0005017 A1 * | 1/2007 | Alchas et al. | 604/117 |
| 2007/0118077 A1 * | 5/2007 | Clarke et al. | 604/117 |
| 2007/0185460 A1 | 8/2007 | Vedrine et al. | |
| 2009/0234288 A1 * | 9/2009 | Fischer | 604/117 |

FOREIGN PATENT DOCUMENTS

| | | | |
|---|---|---|---|
| EP | 1289587 B1 * | 3/2005 | A61M 5/32 |
| EP | 1930038 | 6/2008 | |
| JP | 2001507956 A | 6/2001 | |
| JP | 2002-360695 | 12/2002 | |
| JP | 2003534105 A | 11/2003 | |
| JP | 2005527249 A | 9/2005 | |
| JP | 2006-517129 A | 7/2006 | |
| WO | 0191837 A1 | 12/2001 | |
| WO | 2005018722 | 3/2005 | |
| WO | 2007/061972 A2 | 5/2007 | |

OTHER PUBLICATIONS

Japanese Official Notice of Final Decision of Rejection dated May 12, 2015.

* cited by examiner

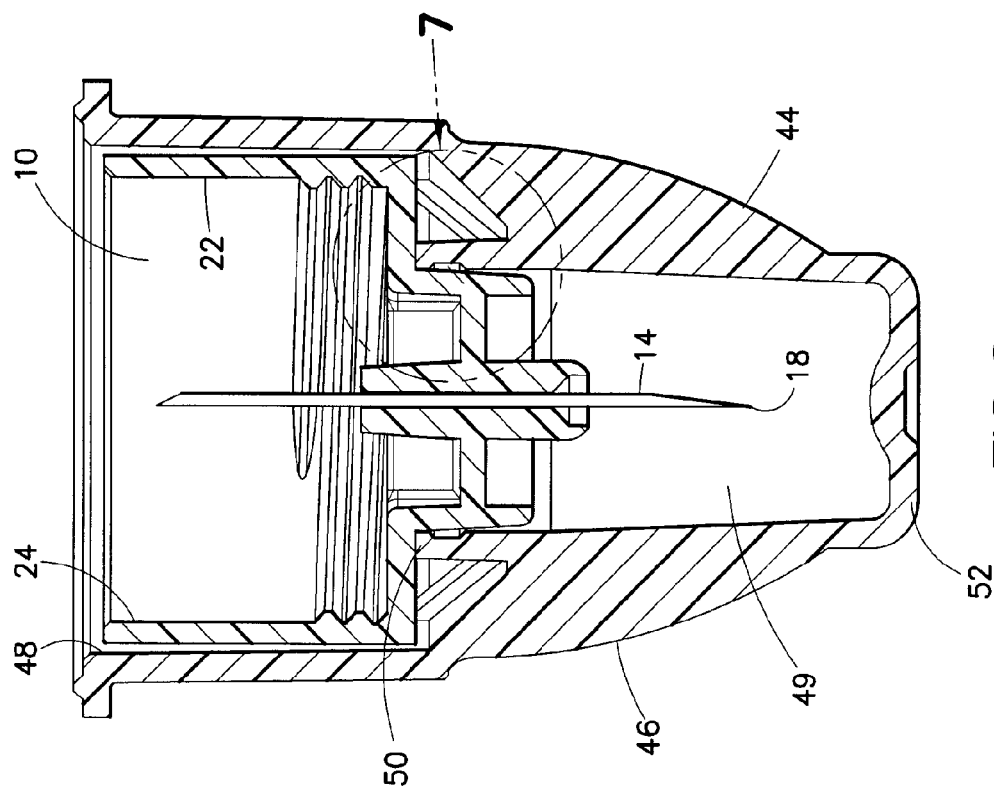
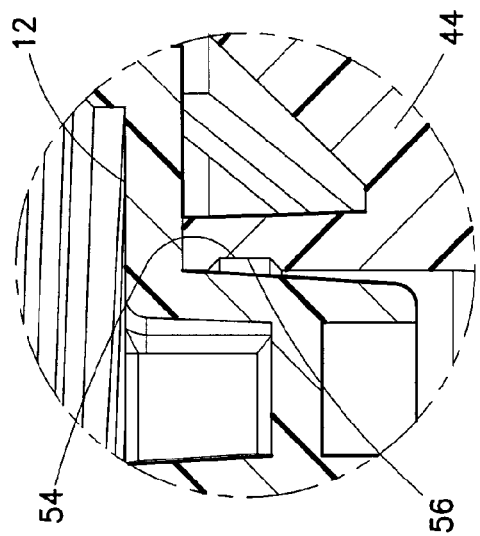

PEN NEEDLE ASSEMBLY FOR DELIVERING DRUG SOLUTIONS

FIELD OF THE INVENTION

This invention relates to pen needle assemblies and, more particularly, to pen needle assemblies for delivering drug suspensions.

BACKGROUND OF THE INVENTION

Pen needle assemblies are well known in the art. To minimize discomfort, pen needle assemblies typically use needles in the range of 29 to 31 gauge. Where a pen injector is used to mix or reconstitute substances into a solution for delivery, thin needles, such as those in the range of 29 to 31 gauge, may be susceptible to clogging by agglomerations which result from re-suspension or incomplete mixing of the substances.

SUMMARY OF THE INVENTION

In one aspect, a pen needle assembly is provided herein which includes a hub, and a needle fixed to the hub, the needle having proximal and distal ends with a lumen extending therebetween. The needle extends distally from the hub to define an exposed length between the distal end of the needle and the hub in the range of about 5.0 to 9.0 mm. The hub defines a post formed about the needle, the post having a distally-facing first skin engaging surface. The exposed length of the needle extends distally from the first skin engaging surface. The hub also defines a distally-facing second skin engaging surface which at least partially circumscribes the first skin engaging surface. The second skin engaging surface being located proximally of the first skin engaging surface. Advantageously, with the subject invention, a pen needle assembly is provided having two skin engaging surfaces which provide stability in achieving subcutaneous injections.

These and other features of the invention will be better understood through a study of the following detailed description and accompanying drawings.

BRIEF DESCRIPTION OF THE DRAWINGS

FIG. 6 is a cross-section showing a pen needle assembly formed in accordance with the subject invention in a packaged state; and FIG. 7 is an enlarged view taken from section 7 of FIG. 6.

DETAILED DESCRIPTION OF THE INVENTION

Figure 1:
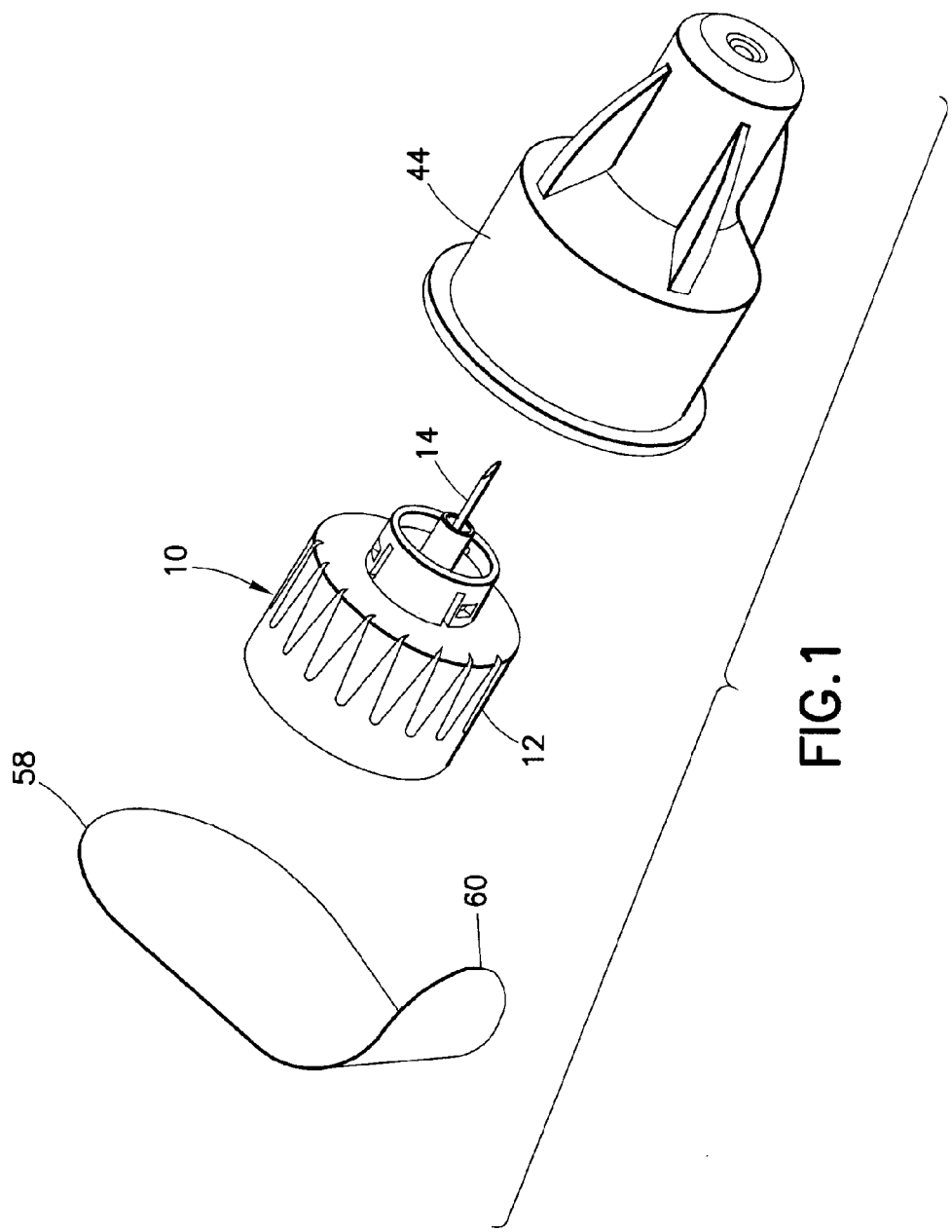
FIG. 1 is an exploded view showing a pen needle assembly formed in accordance with the subject invention along with usable packaging.

With reference to the Figures, a pen needle assembly is shown and generally designated with the reference numeral 10. The pen needle assembly 10 is useable with various pen injectors for administering medicament. The pen needle assembly 10 is particularly well-suited to administer medicament which is mixed into a solution inside the associated pen injector, such as by re-constitution or mixing of two or more components (wet or dry), such as liquid and solid powder of particles, and/or medicament having particles in the formulation suspension. In either case, particles or particle agglomerations may be found in the medicament which may partially or wholly clog the lumen of a prior art administering needle. The pen needle assembly 10 provides an arrangement for delivering the suspension through minimizing the clogging of a needle lumen.

The pen needle assembly 10 generally includes a hub 12 and a needle 14. The needle 14 is fixed to the hub 12 by any known technique, e.g., adhesion, and includes a proximal end 16, a distal end 18 and a lumen 20 extending therebetween.

As used herein, the term "proximal", and derivatives thereof, shall refer to a direction away from a patient during use (i.e., the non-patient end), and the term "distal", and derivatives thereof, shall refer to a direction towards a patient during use (i.e., the patient end).

The hub 12 includes a body 22 which is preferably formed of a polymeric material, e.g. thermoplastic. The body 22 includes an open proximal end 24 which exposes the proximal end 16 of the needle 14. Preferably, the pen needle assembly 10 is removably mountable onto a medical pen injector I. This permits replacement of the pen needle assembly in allowing multiple injections to be administered by the pen injector I. To this end, mounting features 26 are formed on the body 22 for engaging cooperating mounting features F on the pen injector I. The mounting features 26 and F may be of any known type including cooperating threads, mechanical features (e.g., bayonet-type lock) and/or surface configurations, such as Luer surfaces. Alternatively, the hub 12 may be non-removably fixed to, or formed integrally with, the pen injector I. This configuration is useable with a single-use injector which is disposed of after one injection.

The proximal end 16 of the needle 14 is sized so as to access medicament M contained within the pen injector I with the hub 12 being mounted to the pen injector I. Typically, the medicament M will be housed within a reservoir or cartridge accommodated within the pen injector with a septum S forming a seal at the distal end thereof. The proximal end 16 is sufficiently sized to pierce through the septum S to access the medicament M with the hub 12 being mounted to the pen injector I. The medicament M may have clumps or agglomerations A floating therein.

The pen needle assembly 10 is configured to administer an injection of the medicament M into the subcutaneous region of a patient's skin. In addition, the pen needle assembly 10 is configured to minimize clogging in the lumen 20 resulting from insufficient depth of injection (i.e., clogging caused by attempted injection into the dermis/epidermis layer). With the pen needle assembly 10, an injection may be administered in the subcutaneous region with minimal concern for clogging of the lumen 20.

The needle 14 has an exposed length L1 which is defined between the distal end 18 of the needle 14 and the hub 12. The exposed length L1 is the portion of the needle 14 that extends distally from the hub 12 and that may be inserted into the patient during an injection. The exposed length L1 is in the range of about 5.0 to 9.0 mm.

In addition, a beveled surface 28 extends proximally from the distal end 18 of the needle 14 in which distal opening 30 is defined. The lumen 20 terminates at the distal opening 30.

As will be appreciated by those skilled in the art, the beveled surface 28 may include various configurations including having multiple facets or bevels with the surfaces being of various configurations, including being partially or wholly planar and/or arcuate. The beveled surface 28 provides the distal end 18 of the needle 14 with a sharpened configuration for insertion into a patient.

Length L2 of the needle 14 corresponds to the length of needle 14 over which the beveled surface 28 extends. The length L2 is preferably in the range of 30%-60% of the exposed length L1. The length L2 is measured along the longitudinal axis of the needle 14 and not along the length of the beveled surface 28. The length L2, being in the range of 30%-60% of the exposed length L1, provides the distal opening 30 with an elongated shape that is minimally susceptible to clogging in the lumen 20 by any of the agglomerations A formed in the medicament M. It is additionally preferred that the needle 14 be of 25 gauge or larger in size, more preferably in the range of 20-25 gauge. With the needle 14 being of 25 gauge or larger in size, the lumen 20 is larger in cross-sectional size than a lumen of typical prior art pen needles (typical prior art pen needles being in the range of 29-31 gauge). With the needle 14 being of a larger gauge (25 gauge or larger in size), the lumen 20 is better configured to deliver the medicament M as a suspension (e.g., reconstituted or mixed solution) in being less susceptible to clogging of the lumen 20 by any of the agglomerations A formed in the medicament M.

In addition, to achieve a subcutaneous injection, it is preferred that the body 22 of the hub 12 define a post 32 about the needle 14. The post 32 includes a distally-facing first skin engaging surface 34, which is defined about the needle 14 continuously or discontinuously. The first skin engaging surface 34 acts as a stop against excessive insertion of the needle 14 into the patient. Preferably, the exposed length L1 is defined between the distal end 18 of the needle 14 and the first skin engaging surface 34. It is preferred that the post 32 be limited in its outer diameter so as to be smaller than the overall diameter or footprint of the body 22. Preferably, the first skin engaging surface 34 radiates outwardly from the needle 14 and terminates at an outer diameter D1, which more preferably is 0.121".

Figure 2:
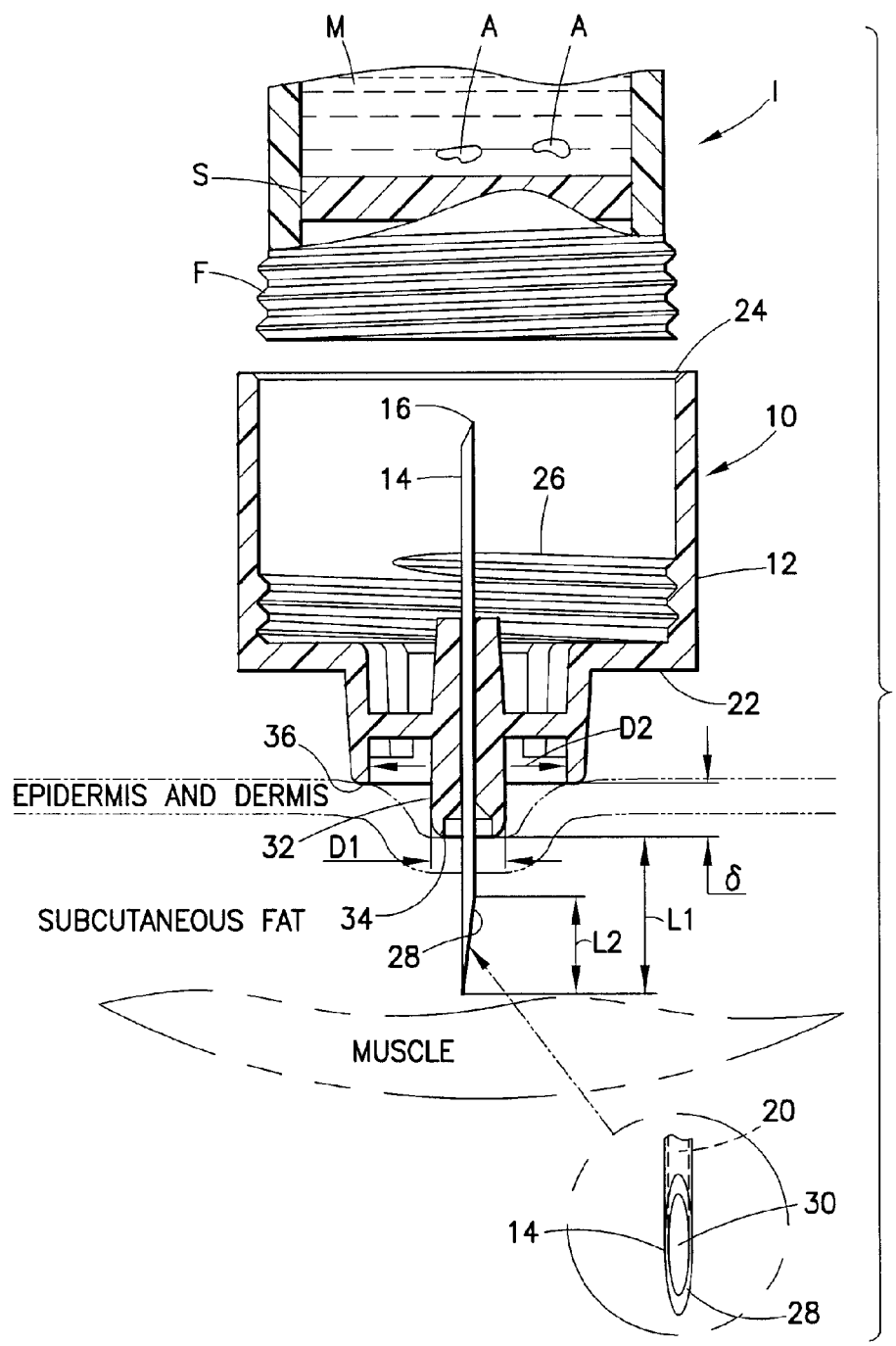
FIG. 2 is a cross-sectional schematic showing an injection formed with a pen needle assembly formed in accordance with the subject invention.

It is further preferred that the hub 12 defines a distally-facing second skin engaging surface 36 which is spaced radially outwardly from, and at least partially circumscribes, the first skin engaging surface 34. The second skin engaging surface 36 is located proximally of the first skin engaging surface 34 so as to define an offset 6 which is preferably in the range of 0.07"-0.10". As shown in FIG. 2, the first skin engaging surface 34 provides a focused point of contact against a patient's skin, which results in some deflection thereof. The second skin engaging surface 36 is spaced radially outwardly and rearwardly, by the offset δ, so as to provide a second hard stop against excessive insertion of the needle 14 into a patient's skin. The second skin engaging surface 36 provides stability to the pen needle assembly 10 during injection. Due to the limited diameter of the first skin engaging surface 34, there may be limited engagement with a patient's skin with insufficient stability for the injection. The second skin engaging surface 36 adds stability.

Figure 3:
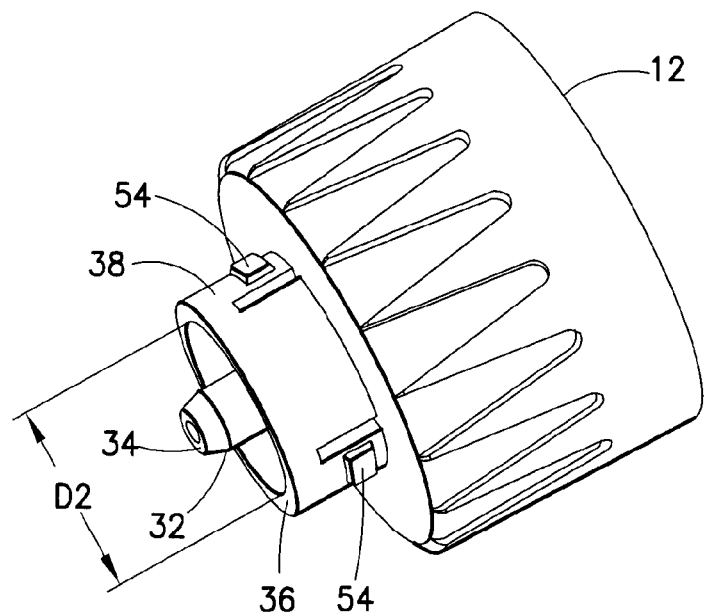
FIGS. 3 and 4 show different configurations of a second skin engaging surface usable with a pen needle assembly in accordance with the subject invention.
Figure 4:
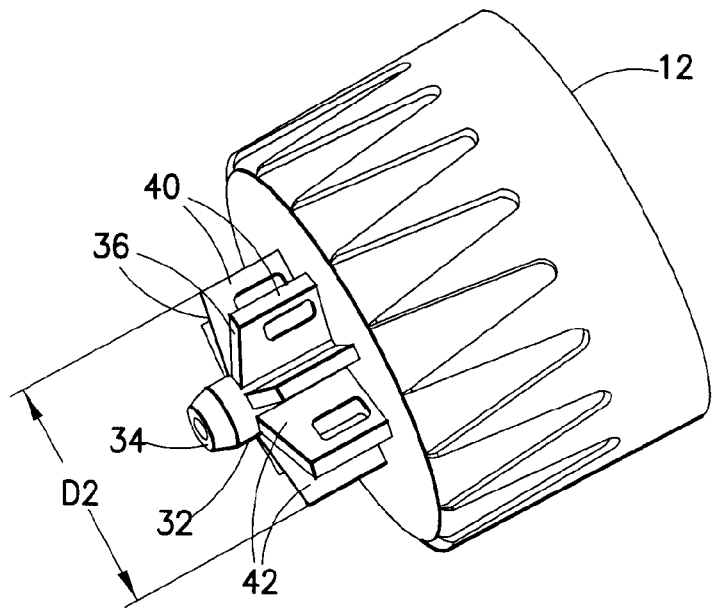

With reference to FIGS. 3 and 4, the second skin engaging surface 36 may be defined by various configurations which are continuous or discontinuous. With reference to FIG. 3, the second skin engaging surface 36 is defined with an annular shape at the end of wall 38 which completely circumscribes the post 32. The second skin engaging surface 36 preferably defines a diameter D2 of 0.340". In the embodiment of FIG. 3, the diameter D2 coincides with the inner edge of the second skin engaging surface 36. With reference to FIG. 4, the second skin engaging surface 36 may be defined over a series of fins 40 which radiate outwardly from the post 32. Spaces 42 are located between the fins 40. The fins 40 are shaped and positioned so that collectively the second skin engaging surface 36 may be defined thereby which limits insertion of the needle 14 into the patient's skin, particularly to achieve a subcutaneous injection. With the embodiment of FIG. 4, the fins 40 may terminate radially outwardly at the diameter D2 so that the diameter D2 coincides with the outer edge of the second skin engaging surface 36. In any regard, it is preferred that the diameter D2 be defined along a free edge of the second skin engaging surface 36 where, adjacent thereto, skin may be deflected or deformed. With the embodiment of FIG. 3, the diameter D2 coincides with an inner free edge of the second skin engaging surface 36, while in the embodiment of FIG. 4, the diameter D2 coincides with an outer free edge of the second skin engaging surface 36.

As shown in FIG. 2, the pen needle assembly 10 is intended for injections administered generally perpendicularly to a patient's skin.

Preferably, the ratio of the diameter D1 to the diameter D2 (D1/D2 ratio) is in the range of 0.25 to 0.58, more preferably the ratio is 0.36. It has been found that with these ratios, acceptable skin tension is created at the site of the injection with good stability. It has been found that if the diameter D2 is too large, insufficient skin tension is created and a shallow injection may result; if the diameter D2 is too small, there may be a lack of stability for injection, with less perpendicularity (which is desired) and a shallow injection resulting.

Figure 5:
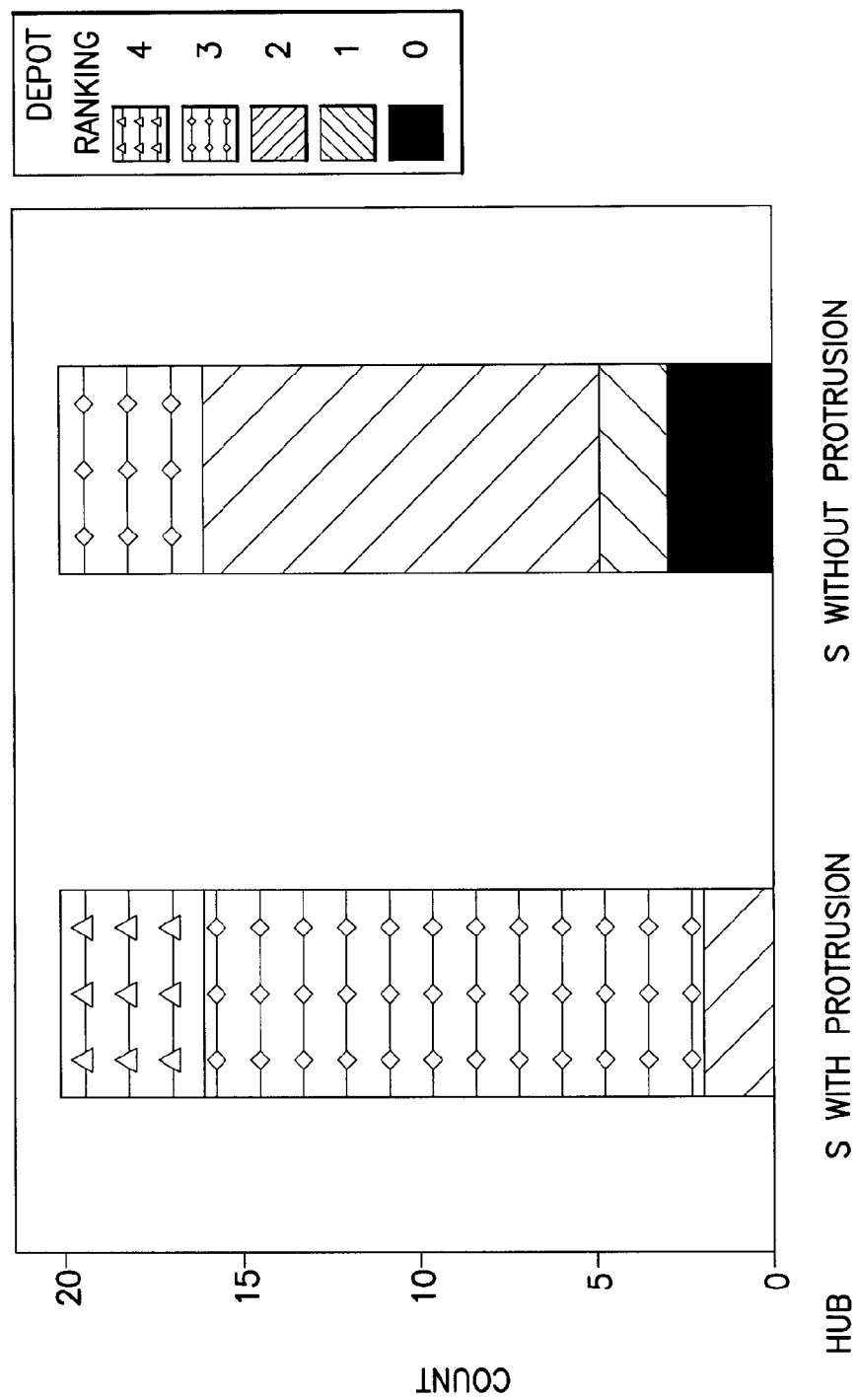
FIG. 5 is a chart showing test results.

With reference to FIG. 5, testing was conducted to evaluate the performance of subcutaneous injections with the pen needle assembly 10. The testing was conducted on a swine animal model, and it is believed that similar or same results will be achieved in injections on humans. The left hand column of FIG. 5 represents test results from using the pen needle assembly 10 as shown in FIG. 2, with the post 32 defining the first skin engaging surface 34 and the second skin engaging surface 36 being proximally set back by the offset δ. More specifically, the needle 14 used for this test was of a 23 gauge type with the offset δ being 0.09", the diameter D1 being 0.121", the exposed length L1 being 7 mm, and the length L2 being 3 mm. In addition, the second skin engaging surface 36 had its inner edge coincide with the diameter D2 being 0.340".

With respect to the results, the injections were observed and ranked: a ranking of 4 corresponds to a deep subcutaneous injection; a ranking of 3 corresponds to a subcutaneous injection; a ranking of 2 corresponds to a shallow subcutaneous injection; a ranking of 1 corresponds to an intradermal injection; and, a ranking of 0 corresponds to a needle clogged by the dermis/epidermis. As can be seen in the left column, with the pen needle assembly 10 of the subject invention, repeated subcutaneous injections were achieved without clogging.

In particular, with reference to FIG. 5, using the pen needle assembly 10 of the subject invention, two shallow subcutaneous injections were achieved; fourteen subcutaneous injections were achieved; and, four deep subcutaneous injections were achieved. No clogging or intradermal injections were experienced.

The right hand column of FIG. 5 represents a pen needle assembly which had the same parameters as discussed above with respect to the first set of test results but was without the offset δ between the first and second skin engaging surfaces 34, 36 (i.e., the first and second skin engaging surfaces 34, 36 are coplanar). As can be seen, the majority of the injections were of the shallow subcutaneous type with a number of clogged needles also being achieved. In particular, three clogged needles were experienced; two intradermal injections were achieved; eleven shallow subcutaneous injections were achieved; and, four subcutaneous injections were achieved. The clogged needles resulted from excessively shallow needle insertion with failed injection into the dermis/epidermis; the needles were sufficiently clogged by the dermis/epidermis to not perform an injection.

As can be seen in FIG. 5, with the pen needle assembly 10 of the subject invention, repeated subcutaneous injections without clogging by the dermis/epidermis may be achieved. Subcutaneous injections as referred to herein are differentiated from shallow subcutaneous injections and deep subcutaneous injections. A subcutaneous injection is administered in a central area of the subcutaneous layer. It is desired to achieve insertion at this depth, rather than in a shallow or deep subcutaneous region where injections therein may coincide with the dermis/epidermis or muscle regions, respectively, of the patient. With the pen needle assembly 10 of the subject invention, medicament, which may be in suspension or prone to agglomeration, may be repeatedly delivered into the subcutaneous region with low susceptibility to clogging.

The pen needle assembly 10 may be packaged for use, as shown in FIGS. 1, 6 and 7. In particular, a rigid shell 44 may be provided sized to accommodate the pen needle assembly 10 therein with at least a portion of the needle 14, preferably at least the distal end 18 of the needle 14, being covered. Preferably, the shell 44 has a cup-shaped body 46 with an open proximal end 48 and an interior 49 into which the pen needle assembly 10 may be seated. To prevent excessive insertion of the pen needle assembly 10 into the body 46 during packaging, shoulder 50 may define a reduced-diameter region in the interior 49 which limits the extent of insertion of the pen needle assembly 10 into the body 46. As shown in FIG. 6, it is preferred that minimal clearance be defined between the shoulder 50 and the second skin engaging surface 36 so as to limit passage thereby of contaminants. Sterility of the exposed length L1 of the needle 14 may be better maintained in this manner. It is preferred that the proximal end 24 of the body 22 be exposed when seated in the body 46 such that the pen injector I may be mounted to the pen needle assembly 10 with it being contained within the shell 44. It is also preferred that the distal end 52 of the shell 44 be spaced from the distal end 18 of the needle 14 with the pen needle assembly 10 being seated within the body 46. In this manner, blunting of the needle 14 and inadvertent piercing of the shell 44 by the needle 14 may be avoided.

The shell 44 may be maintained on the pen needle assembly 10 in any known manner which permits releasable retainment of the shell 44 on the hub 12, including by frictional interengagement, frangible connection, mechanical connection and/or fusion or adhesion, such as spot fusion or adhesion. The force of retention for maintaining the shell 44 in the hub 12 should be great enough to prevent separation of the shell 44 from the hub 12 during normal transporting and storage, which may involve jarring or other force application to the combined package. It is preferred that the shell 44 be re-mountable onto the hub 12 after use (i.e., after an injection) so as to cover the needle 14 in a post-use state. It is preferred that the configuration for releasable retainment permit re-mounting of the shell 44 and retention thereof on the hub 12. In this manner, the pen needle assembly 10 may be disposed of with the needle 14 in a used state being covered.

Preferably, as shown in FIG. 3, one or more resilient snaps 54 may be provided on the hub 12 which are received in snap engagement in corresponding snap recesses 56 formed on the shell 44, as shown in FIGS. 6 and 7. In a packaged state, as shown in FIGS. 6 and 7, the inherent resilience of the interengagement of the snaps 54 and the snap recesses 56 provide sufficient retaining force for holding the shell 44 onto the hub 12. The inherent resilience, however, is surmountable to permit disengagement of the snaps 54 from the snap recesses 56 in allowing separation of the shell 44 from the hub 12 to permit use. The shell 44 may be re-mounted onto the hub 12 after use with the snaps 54 and the snap recesses 56 being caused to re-engage. As will be appreciated by those skilled in the art, the snaps 54 and the snap recesses 56 may be formed on the hub 12/and or the shell 44.

It is preferred that an audible signal be generated upon the shell 44 being properly mounted onto the hub 12 in entering the retained state therewith. For example, the snaps 54 may have sufficient inherent resilience so as to generate a click, or other audible signal, upon snap engaging the snap recesses 56.

The pen needle assembly 10 is preferably mounted onto the pen injector I prior to any necessary preparation of the medicament M, such as by mixing or reconstituting components found in the pen injector I. It is preferred that a sufficiently strong retaining force be provided for the shell 44 on the hub 12 so as to retain the shell 44 on the hub 12 during any shaking or other agitation of the pen injector I in preparing the medicament M. The agitation may include tapping the shield 44 against a surface. The retaining force needs to be sufficiently strong to prevent separation under such conditions. Subsequent manual removal of the shield 44 from the hub 12, however, must be permitted to allow priming of the needle 14 and subsequent injection.

The inherent resilience of the retaining force may also be sufficiently strong to permit rotational force applied to the shell 44 to be transmitted to the hub 12 in mounting the pen needle assembly 10 onto the pen injector I, particularly where the mounting features 26 and F are cooperating threads.

A barrier sheet or film 58 may be also provided to be applied in removable securement across the proximal end 48 of the shell 44 to wholly enclose, with the shell 44, the pen needle assembly 10 in a packaged state. Preferably, the sheet 58 provides a sterility barrier. The pen needle assembly 10 may be sterilized prior to packaging within the shell 44 or while inside the shell 44. The sheet 58 may be secured to the shell 44 using known techniques, such as adhesion or fusion. A grip 60 may be provided to extend from the sheet 58 to facilitate removal thereof.

What is claimed is:
1. A pen needle assembly comprising:
a hub; and
a needle fixed to said hub, said needle having proximal and distal ends with a lumen extending therebetween, said needle having a substantially uniform outer diameter;
wherein said needle extends distally from said hub to define an exposed length between said distal end of said needle and said hub in the range of about 5.0 to 9.0 mm to facilitate a subcutaneous injection;
wherein said hub defines a post formed about said needle, said post having a distally-facing first skin engaging surface, said exposed length of said needle extending distally from said first skin engaging surface; and wherein said hub defines an annular wall defining a radially facing surface and a distally-facing second skin engaging surface which at least partially circumscribes said first skin engaging surface, said second skin engaging surface being located at a fixed distance proximally of said first skin engaging surface;

wherein said second skin engaging surface is continuous;

wherein said second skin engaging surface is radially displaced from said first skin engaging surface;

wherein said hub defines a cavity between said first skin engaging surface and said second skin engaging surface, the cavity comprising a distally facing surface located proximally of said second skin engaging surface; and a rigid shell;

wherein the assembly further comprises at least one snap formed on one of the radially facing surface or the rigid shell, adapted to be received and retained in a snap recess formed in the other of the radially facing surface or the rigid shell.

2. An assembly as in claim 1, wherein said needle is of 25 gauge or larger in size.

3. A pen needle assembly as in claim 2, wherein said needle is of a gauge in the range of 20-25.

4. A pen needle assembly as in claim 1, wherein said second skin engaging surface is located proximally of said first skin engaging surface in the range of 0.07"-0.10".

5. A pen needle assembly as in claim 1, wherein said needle includes a beveled surface extending proximally from said distal end, said lumen terminating at a distal opening defined in said beveled surface, the length of said needle corresponding to the beveled surface being in the range of 30%-60% of said exposed length.

6. A pen needle assembly as in claim 1, wherein said first skin engaging surface radiates outwardly from said needle and terminates at a first diameter.

7. A pen needle assembly as in claim 6, wherein said second skin engaging surface defines a second diameter, the ratio of said first diameter to said second diameter is in the range of 0.25 to 0.58.

8. A pen needle assembly as in claim 7, wherein the ratio of said first diameter to said second diameter is 0.36.

9. A pen needle assembly as in claim 7, wherein an inner edge of said second skin engaging surface defines said second diameter.

10. A pen needle assembly as in claim 7, wherein an outer edge of said second skin engaging surface defines said second diameter.

11. A pen needle assembly comprising:

a hub having first and second skin engaging surfaces defining an annular space having a distally facing surface therebetween, said second skin engaging surface formed on an annular wall of the hub and continuously circumscribing and being located at a fixed distance radially outward of said first skin engaging surface and proximally of said first skin engaging surface, said distally facing surface of said annular space being located proximally of said second skin engaging surface, said hub having a cavity to receive an injection device, said hub being unitarily formed as a single piece; and a needle fixed to said hub, said needle having proximal and distal ends with a lumen extending therebetween, said needle having a substantially uniform outer diameter;

wherein said needle extends distally from said hub to define an exposed length between said distal end of said needle and said hub in the range of about 5.0 to 9.0 mm to facilitate a subcutaneous injection;

wherein said needle includes a beveled surface extending proximally from said distal end, said lumen terminating at a distal opening defined in said beveled surface, the length of said needle corresponding to the beveled surface being in the range of 30%-60% of said exposed length; and a rigid shell;

wherein the assembly further comprises at least one snap formed on one of the annular wall or the rigid shell, and adapted to be received and retained in a snap recess formed in the other of the radially facing surface or the rigid shell.

12. An assembly as in claim 11, wherein said needle is of 25 gauge or larger in size.

13. A pen needle assembly as in claim 12, wherein said needle is of a gauge in the range of 20-25.

* * * * *